United States Patent
Schweizer

(10) Patent No.: US 11,249,596 B2
(45) Date of Patent: Feb. 15, 2022

(54) PROVIDING AN OUTPUT SIGNAL BY A TOUCH-SENSITIVE INPUT UNIT AND PROVIDING A TRAINED FUNCTION

(71) Applicant: Siemens Healthcare GmbH, Erlangen (DE)

(72) Inventor: Hans Schweizer, Plattling (DE)

(73) Assignee: Siemens Healthcare GmbH, Erlangen (DE)

(*) Notice: Subject to any disclaimer, the term of this patent is extended or adjusted under 35 U.S.C. 154(b) by 62 days.

(21) Appl. No.: 16/891,930

(22) Filed: Jun. 3, 2020

(65) Prior Publication Data

US 2020/0393951 A1    Dec. 17, 2020

(30) Foreign Application Priority Data

Jun. 12, 2019 (DE) .......................... 102019208522.9
Jun. 19, 2019 (DE) .......................... 102019208903.8

(51) Int. Cl.
*G06F 3/041* (2006.01)
*G06F 3/01* (2006.01)
(Continued)

(52) U.S. Cl.
CPC .......... *G06F 3/04186* (2019.05); *G06F 3/017* (2013.01); *G06N 3/084* (2013.01); *G06N 20/00* (2019.01); *G16H 40/60* (2018.01)

(58) Field of Classification Search
CPC ...... G06F 3/041; G06F 3/04186; G06F 3/017; G06F 3/045; G06F 3/042; G16H 40/60;
(Continued)

(56) References Cited

U.S. PATENT DOCUMENTS 7,995,036 B2 * 8/2011 Perski ................. G06F 3/04162
345/173
8,786,560 B1   7/2014 Khafizov
(Continued)

FOREIGN PATENT DOCUMENTS

CN    106201292 A    12/2016
DE    102012218308 A1    5/2013
(Continued)

OTHER PUBLICATIONS

Bunke, J., F. Kleinwachter, and P. Walerius. "Identification of disturbed nonlinear systems with artificial neural networks." Automatisierungstechnik 45.4 (1997): 181-191.
(Continued)

*Primary Examiner* — Pegeman Karimi
(74) *Attorney, Agent, or Firm* — Lempia Summerfield Katz LLC

(57) ABSTRACT

A computer-implemented method for providing an output signal by a touch-sensitive input unit includes detecting a sensor signal, wherein the sensor signal is time-resolved and spatially resolved with respect to a surface of the touch-sensitive input unit, and wherein the sensor signal includes unwanted-signal components. The method also includes determining the output signal by applying a trained function to input data, wherein the input data is based on the sensor signal, wherein the output signal is time-resolved and spatially resolved with respect to the surface of the touch-sensitive input unit, wherein at least one parameter of the trained function is based on a comparison with a sensor signal in the absence of unwanted-signal components. The method also includes providing the output signal.

20 Claims, 6 Drawing Sheets

(51) Int. Cl.
*G06N 3/08* (2006.01)
*G06N 20/00* (2019.01)
*G16H 40/60* (2018.01)

(58) Field of Classification Search
CPC ........ G06N 20/00; G06N 3/084; G06K 11/06; G08C 21/00
See application file for complete search history.

(56) References Cited

U.S. PATENT DOCUMENTS

| | | | |
|---|---|---|---|
| 9,483,152 B2* | 11/2016 | Chang | G06F 3/04184 |
| 2004/0095333 A1* | 5/2004 | Morag | G06F 3/0418 |
| | | | 345/173 |
| 2009/0006292 A1 | 1/2009 | Block | |
| 2010/0216447 A1 | 8/2010 | Park | |
| 2012/0287056 A1 | 11/2012 | Ibdah | |
| 2013/0106740 A1 | 5/2013 | Yilmaz | |
| 2013/0234980 A1* | 9/2013 | Wang | G06F 3/041 |
| | | | 345/174 |
| 2013/0326395 A1 | 12/2013 | Oh | |
| 2014/0062893 A1* | 3/2014 | Kawalkar | G06F 3/04186 |
| | | | 345/173 |
| 2014/0282280 A1 | 9/2014 | Pack | |
| 2014/0300559 A1 | 10/2014 | Tanimoto | |
| 2016/0041683 A1 | 2/2016 | Ma | |
| 2016/0048257 A1 | 2/2016 | Church | |
| 2016/0077664 A1 | 3/2016 | Harrison | |
| 2016/0092022 A1 | 3/2016 | Lee | |
| 2017/0235426 A1 | 8/2017 | Peterson | |
| 2018/0059865 A1 | 3/2018 | Qu | |
| 2018/0213126 A1 | 7/2018 | Fleizach | |
| 2018/0314387 A1 | 11/2018 | Hwang | |

FOREIGN PATENT DOCUMENTS

| | | |
|---|---|---|
| DE | 102013215809 A1 | 2/2015 |
| EP | 2523085 A1 | 11/2012 |
| JP | 2017139017 A | 8/2017 |
| WO | WO2014201648 A1 | 12/2014 |

OTHER PUBLICATIONS

German Office Action for German Application No. 10 2019 208 903.8 dated Feb. 12, 2020.

Prestop—Products: "Touch technologies compared"; Screenshot from Aug. 22, 2018. pp. 1-11 https://web.archive.org/web/20180822084226/http://prestopproducts.com/touch-skins/touch-technologies-compared/.

Schweizer, Hans: "PCAP touch screen with additional signal acquisition for the operation of safety-critical functions in a medical technology device" Prior Art Journal; vol. 13; pp. 48-49, 2015 // DOI: 10.4421/PAPDEOTT004435—ISBN: 978-3-945188-16-3.

* cited by examiner

PROVIDING AN OUTPUT SIGNAL BY A TOUCH-SENSITIVE INPUT UNIT AND PROVIDING A TRAINED FUNCTION

The present patent document claims the benefit of German Patent Application No. 10 2019 208 522.9, filed Jun. 12, 2019, and German Patent Application No. 10 2019 208 903.8, filed Jun. 19, 2019, which are both hereby incorporated by reference.

TECHNICAL FIELD

The present disclosure relates to a computer-implemented method for providing an output signal by a touch-sensitive input unit. The disclosure also relates to a computer-implemented method for providing a trained function, to a provider unit, to a medical apparatus, to a training system, to a computer program product, and to a computer-readable storage medium.

BACKGROUND

It is known from the prior art that many medical apparatuses, (e.g., C-arm X-ray apparatuses, magnetic resonance systems, or computed tomography systems), include touch-sensitive input units. These may be used to achieve control by an input by an operator at the touch-sensitive input unit.

The input units may be resistive input units, capacitive input units, optical input units (e.g., infrared-based input units), surface-wave based input units, ultrasound-based input units, or combinations thereof. In the case of a resistive input unit, when touching occurs, an electrical resistance may be changed, in particular an electrical contact is made, in particular as a result of a mechanical deformation of a transparent outer layer. The touch may be detected in a spatially resolved manner by virtue of a plurality of electrically conducting contact tracks arranged in a contact layer, which is located in particular beneath the transparent outer layer.

Capacitive input units may have better ergonomics than resistive input units. In particular, in the case of projected capacitive touch (PCAP) input units, the input unit may include two layers which are electrically isolated from one another. The first layer may be embodied here as a sensor, and the second layer as a driver. In addition, at least the layer embodied as a sensor may be divided into a plurality of segments, which may be electrically isolated from one another, and each of which may be assigned a spatial position. It is thereby possible for the layer embodied as a sensor to be spatially resolved. In addition, the electrical field produced between the second layer and an operating object, (e.g., an input pen and/or finger of the operator), may be projected through a transparent outer layer located on the first layer. Thus, touching and/or approaching may cause a change in the capacitance at the position of the touch, with the first layer able to detect this change in a spatially resolved manner.

The known touch-sensitive input units may be configured to generate a sensor signal that corresponds to an intended input at the input unit.

In particular, when using touch-sensitive input units in a medical environment, (e.g., in an operating theater), there may be many interference sources that may impede correct recognition of an intended input at the input unit and/or may lead to an erroneous input. For instance, as a result of electromagnetic fields from medical apparatuses, in particular located in the same room, (e.g., a defibrillator), and/or from surgical apparatuses, (e.g., an electrocautery pen and/or a lithotripter), and/or from other electrical apparatuses, coupling-in may occur at the touch-sensitive input unit. In addition, in particular in the surgical environment, electrically conducting fluids, (e.g., water, physiological saline solution, ultrasound gel, blood, or combinations thereof), may result in an erroneous input at the touch-sensitive input unit. The sensor signal from the input unit may therefore include a very large number of errors and may be unsuitable for controlling a medical apparatus.

SUMMARY AND DESCRIPTION

The object of the disclosure is to make reliable error-suppression possible for a sensor signal from a touch-sensitive input unit.

This object is achieved by a method for providing an output signal by a touch-sensitive input unit, by a method for providing a trained function, by a provider unit, by a medical apparatus, by a training system, by computer program products, and by computer-readable storage media as disclosed herein.

Achieving the object is described below both with reference to the claimed devices and with reference to the claimed method. Features, advantages, or alternative embodiments mentioned in this connection may also be applied to the other claimed subject matter, and vice versa.

Furthermore, achieving the object is described both with reference to methods and devices for providing an output signal by a touch-sensitive input unit, and with reference to methods and devices for providing trained functions. Features and alternative embodiments of data structures and/or functions in methods and devices for providing an output signal by a touch-sensitive input unit may also be applied to analogous data structures and/or functions in methods and devices for providing trained functions. The analogous data structures may be identified in particular by the use of the prefix "training". In addition, the trained functions used in methods and devices for providing an output signal by a touch-sensitive input unit may be adjusted and/or provided in particular by methods and devices for providing trained functions.

A first aspect of the disclosure relates to a method for providing an output signal by a touch-sensitive input unit. According to the method, a sensor signal is detected, wherein the sensor signal is time-resolved, and spatially resolved with respect to a, in particular predetermined, surface of the touch-sensitive input unit. In addition, the sensor signal includes unwanted-signal components. The output signal is determined by applying a trained function to input data. The input data is based on the sensor signal. In addition, the output signal is time-resolved, and spatially resolved with respect to the surface of the touch-sensitive input unit. Moreover, at least one parameter of the trained function is based on a comparison with a sensor signal in the absence of unwanted-signal components. The output signal is then provided.

The touch-sensitive input unit may include a touch-sensitive input field, wherein the input field may be embodied as a, (e.g., projected), capacitive input field; an optical, (e.g., infrared-based), input field; a surface-wave based input field; an ultrasound-based input field; a resistive input field; or a combination thereof.

The sensor signal advantageously includes an electrical and/or optical signal, which the input unit may generate in the event of an input at the touch-sensitive input unit. An input at the touch-sensitive input unit may be made by an operating object, (e.g., an input pen and/or a finger of an operator).

In addition, detecting the sensor signal may advantageously include receiving the sensor signal. The time-resolved sensor signal may allow for a plurality of inputs to be detected sequentially in time at the touch-sensitive input unit. Furthermore, the spatial resolution of the sensor signal with respect to the surface of the touch-sensitive input unit may allow an input at the input unit to be located exactly. In particular, in combination with the time-resolution and spatial resolution of the sensor signal, it is possible to detect inputs at the touch-sensitive input unit that include, in particular, a movement and/or input gesture. An input gesture may be formed here, for example, by a predetermined sequence in time and/or space of at least one input at the touch-sensitive input unit.

It is particularly advantageous if the surface of the touch-sensitive input unit is predetermined, in particular by parameters, in particular is known. A particularly precise spatial resolution of the sensor signal may hence be achieved, in particular, even for a curved and/or uneven surface of the touch-sensitive input unit. For example, a foldable and/or flexible touch-sensitive input unit may have a curved surface. It is particularly advantageous in this case for precise spatial resolution of the sensor signal if the surface of the input unit is predetermined, in particular by parameters, in particular is known.

The unwanted signals contained in the sensor signal may have, in particular, different causes and/or characteristics from one another. In particular, unwanted-signal components may originate inside the touch-sensitive input unit and may also be produced by an external influence on the touch-sensitive input unit. The unwanted-signal component denotes a component of the sensor signal, (e.g., an additional component and/or a component that is superimposed on other signal components).

In particular, the sensor signal includes, in addition to the unwanted-signal components, a wanted-signal component, which corresponds, (e.g., exclusively), to an, in particular intended, input at the touch-sensitive input unit. In addition, the unwanted-signal component may cause the wanted-signal component to be concealed and/or modified and/or corrupted. In particular, constructive interference, destructive interference, modulation, or a combination thereof may occur between the unwanted-signal component and additional signal components contained in the sensor signal.

A trained function maps input data onto output data. The output data may depend on one or more parameters of the trained function. The one or more parameters of the trained function may be determined and/or adjusted by training. Determining and/or adjusting the one or more parameters of the trained function may be based on a pair composed of training input data and associated training output data, wherein the trained function for generating training mapping data is applied to the training input data. The determining and/or adjusting may be based on a comparison of the training mapping data and the training output data. A trainable function, (e.g., a function containing one or more parameters yet to be adjusted), may also referred to as a trained function.

Other terms for trained function are trained mapping rule, mapping rule containing trained parameters, function containing trained parameters, algorithm based on artificial intelligence, and machine-learning algorithm. An example of a trained function is an artificial neural network, where the edge weights of the artificial neural network are equivalent to the parameters of the trained function. The term "neural net" may also be used instead of the term "neural network". In particular, a trained function may also be a deep artificial neural network (deep neural network). Another example of a trained function is a "support vector machine", and in particular other machine-learning algorithms may also be used as a trained function.

The output signal is advantageously determined by applying the trained function to the input data. Moreover, at least one parameter of the trained function is based on a comparison with a sensor signal in the absence of unwanted-signal components. In particular, the at least one parameter of the trained function may be based on a comparison of an additional output signal, (e.g., a training output signal), with the sensor signal in the absence of unwanted-signal components. The additional output signal may be determined by applying the trained function to input data based on an additional sensor signal. The training output signal may be determined as part of a proposed computer-implemented method for providing a trained function, which is described later. The additional sensor signal may be time-resolved, and spatially resolved with respect to the surface of the touch-sensitive input unit. Furthermore, the additional sensor signal may be detected in the same manner as the previously described signal, e.g., independently thereof in terms of time. In addition, the additional sensor signal may be equivalent to a training sensor signal. Furthermore, the additional sensor signal may include unwanted-signal components. Moreover, the additional output signal, (e.g., the training output signal), may be time-resolved, and spatially resolved with respect to the surface of the touch-sensitive input unit.

It may therefore be achieved that the output signal is additionally time-resolved, and spatially resolved with respect to the surface of the touch-sensitive input unit. Furthermore, the output signal is advantageously based on an error-suppressed signal, which signal corresponds to the, (e.g., detected), sensor signal. Thus, the output signal may include fewer unwanted-signal components than the sensor signal. In addition, the output signal further includes at least one signal component, (e.g., equating to the wanted-signal component), which corresponds to an input at the touch-sensitive input unit.

The error-suppressed sensor signal may have a smaller disparity, (e.g., difference), from the wanted-signal component than the detected sensor signal. In particular, the error-suppressed sensor signal advantageously includes at least one unwanted-signal component fewer than the detected sensor signal. In other words, the error-suppressed sensor signal may be described as a sensor signal that has been cleaned by at least one unwanted-signal component compared with the detected sensor signal. The error-suppressed sensor signal may be additionally time-resolved, and spatially resolved with respect to the surface of the touch-sensitive input unit.

In a further advantageous embodiment, the temporal variation of the sensor signal may relate to a time period before and/or after an input at the touch-sensitive input unit. An input at the touch-sensitive input unit may be understood to mean that the operating object touches the touch-sensitive input unit directly. The time period before and/or after the input at the touch-sensitive input unit may equate to an approach time stage and/or a distancing time stage for an operating object for the input at the touch-sensitive input unit. It is thereby possible to distinguish unwanted-signal components of the sensor signal particularly reliably from wanted-signal components, which correspond to an input at the touch-sensitive input unit. A temporal variation of an unwanted-signal component, (which is produced in particular by a fluid located on the surface of the touch-sensitive input unit), may, in a time period after the input at the touch-sensitive input unit, advantageously differ from a temporal variation of the signal component corresponding to the input. For example, at the end of the input, (e.g., during a distancing time stage), an operating object may be moved away again from the surface of the touch-sensitive input unit. In contrast, a fluid located on the surface of the touch-sensitive input unit may still persist at least in part on the surface of the touch-sensitive input unit at the end of the input. If the touch-sensitive input unit is embodied as a projected capacitive input field, detecting an operating object may be achieved particularly intuitively, (e.g., as part of the temporal variation of the sensor signal), in a time period before and/or after an input at the touch-sensitive input unit (e.g., hover touch mode).

In a further advantageous embodiment, the unwanted-signal components may be produced by noise and/or by a, in particular electrically conducting, fluid located on the surface of the touch-sensitive input unit. Unwanted-signal components may be produced by noise, for instance caused by energization of the touch-sensitive input unit and/or by sensor noise within the touch-sensitive input unit. A, in particular electrically conducting, fluid located on the surface of the touch-sensitive input unit may produce in particular an erroneous input at the touch-sensitive input unit. The fluid on the surface of the touch-sensitive input unit may produce in particular different characteristics of unwanted-signal components. For instance, a drop of a, in particular electrically conducting, fluid may produce a highly localized and/or point-specific erroneous input at the touch-sensitive input unit, in particular similar to an input by an operator's finger and/or by an input pen. In addition, a plurality of drops of a fluid on the surface of the touch-sensitive input unit may produce a plurality of unwanted-signal components. Furthermore, a film of fluid on the surface of the touch-sensitive input unit may result in an increase in a threshold value of a capacitance change, in particular over a large area of the surface of the touch-sensitive input unit. This may significantly reduce a sensitivity of the touch-sensitive input unit to inputs, in particular to intended inputs.

The unwanted-signal components of the sensor signal that are described here may advantageously be reduced and/or removed by applying the trained function to the input data. The output signal determined in the process may describe an error-suppressed sensor signal, which includes to a lesser extent, and/or no longer includes, the unwanted-signal components of the sensor signal that are produced in particular by noise and/or a fluid located on the surface of the touch-sensitive input unit.

In a further advantageous embodiment, the unwanted-signal component may have a temporal variation, which describes a spreading movement and/or a flow movement of a, (e.g., electrically conducting), fluid on the surface of the input unit. A spreading movement and/or a flow movement of a fluid located on the surface occurs, e.g., when a surface of the touch-sensitive input unit is curved and/or uneven. An unwanted-signal component produced by such a spreading movement and/or flow movement of a fluid on the surface of the touch-sensitive input unit may be identified by taking it into account accordingly as an erroneous input and/or erroneous input gesture.

For a fluid located on the surface of the touch-sensitive input unit, the exact position and/or spatial extent of the fluid is determined advantageously on the basis of the spatial resolution of the sensor signal. In addition, a possible spreading movement and/or flow movement of the fluid may be deduced, in particular, from the predetermined surface of the touch-sensitive input unit. For example, the position and/or spatial extent of the fluid on the surface of the touch-sensitive input unit may be used to ascertain a possible spreading movement and/or flow movement of the fluid, in particular, also in combination with an operating object. Hence, the unwanted-signal component, which is produced in particular by the spreading movement and/or flow movement of a fluid located on the surface of the touch-sensitive input unit, may be ascertained from the position and/or spatial extent of the fluid.

In a further advantageous embodiment, the sensor signal may include an unwanted-signal component from an electromagnetic field at least adjoining the surface of the input unit. Especially in a medical environment, there are numerous medical apparatuses, (e.g., a magnetic resonance system), that are located in immediate spatial proximity to a touch-sensitive input unit. These medical apparatuses may emit electromagnetic radiofrequency fields, which may interfere with the touch-sensitive input unit. When determining the output signal, the errors in the sensor signal may be suppressed particularly reliably by taking into account the unwanted-signal component of an electromagnetic field, which at least adjoins the surface of the input unit, and in particular is coupled-in.

In a further advantageous embodiment, the sensor signal may additionally include at least one motion-sensor signal. The at least one motion-sensor signal may include unwanted-signal components. In addition, the output signal may include at least one motion-sensor output signal, wherein the at least one motion-sensor output signal has fewer unwanted-signal components than the at least one motion-sensor signal. The at least one motion-sensor signal may be generated from at least one motion sensor, which in particular is arranged on the touch-sensitive input unit. The at least one motion sensor is advantageously configured to detect a movement of an operating object and/or further objects and/or fluids on the touch-sensitive input unit. In addition, the at least one motion sensor may be configured to detect an alteration, (e.g., a deflection), at the surface of the touch-sensitive input unit. Moreover, the at least one motion sensor may be configured to detect a tilt and/or inclination of the touch-sensitive input unit about at least one spatial axis. A plurality of motions sensors, (e.g., of different types), such as a radar sensor, an ultrasound sensor, a camera system, an electromagnetic sensor, an optical sensor, or a combination thereof, may advantageously each generate a motion-sensor signal. The sensor signal may include the plurality of motion-sensor signals. For instance, a motion sensor may be embodied as a camera system that is advantageously configured to identify an operating object, for instance, an input pen and/or a finger of an operator. The identification by the camera system may advantageously include color recognition and/or pattern recognition, in particular, in the visible light spectrum and/or in the infrared region.

In addition, the output signal may advantageously include a plurality of motion-sensor output signals, wherein each of the plurality of motion-sensor output signals may correspond to exactly one of the plurality of motion-sensor signals. Furthermore, an output signal is generated by applying the trained function to the sensor signal including a plurality of motion-sensor signals, wherein the output signal includes a, in particular common, motion output signal. The motion output signal may here advantageously combine the plurality of motion-sensor signals from the plurality of, in particular different, motion sensors.

In particular, for a fluid located on the surface of the touch-sensitive input unit, the at least one motion-sensor signal and/or the motion-sensor output signal may advantageously be used to determine a possible spreading movement and/or flow movement of the fluid. For example, when determining the output signal, the errors in the sensor signal may be suppressed particularly reliably and robustly by the motion-sensor signal and/or the motion-sensor output signal from a motion sensor configured to detect a tilt and/or inclination of the touch-sensitive input unit.

In a further advantageous embodiment, the output signal may be used to control a medical apparatus. In this case, for example, the output signal may be used to control a medical imaging device, (e.g., a magnetic resonance system, a medical X-ray apparatus, a computed tomography system, an ultrasound apparatus, a medical robotic device such as a catheter robot, a component of a medical apparatus such as a patient positioning device, a respiratory device, an anesthesia device, or a combination thereof). A medical apparatus may therefore be controlled particularly reliably and robustly, in particular, in a surgical environment.

By virtue of the output signal additionally being time-resolved, and spatially resolved with respect to the surface of the touch-sensitive input unit, inputs that in particular include a movement and/or input gesture may be described by the output signal and used for controlling the medical apparatus. In addition, compared with the, (e.g., detected), sensor signal, it is possible to achieve far more precise control of the medical apparatus. The output signal may include fewer unwanted-signal components than the sensor signal. This may advantageously prevent errors in operating and/or controlling the medical apparatus, for instance, caused by an unwanted-signal component of the sensor signal that equates to an erroneous input.

In a further advantageous embodiment, a value of an input intention may be ascertained from the output signal. The value of the input intention may be a value in a range from zero to 1, where a value equal to zero corresponds to an unintended input, and a value equal to 1 corresponds to an intended input. Values of the input intention that lie between the values assigned to an unintended and intended input may describe an uncertainty in the determination of the input intention. The value of the input intention may be ascertained by analyzing a temporal and/or spatial variation of the output signal. For instance, an intended input may be identified by a coherent spatial and/or temporal variation and/or a spatial and/or temporal variation that corresponds to a specified input gesture. The value of the input intention may advantageously be determined with greater accuracy and reliability from the output signal than from the sensor signal.

Furthermore, the sensor signal may additionally include at least one motion-sensor signal. In this case, the output signal may include at least one motion-sensor output signal, wherein the value of the input intention may be ascertained from the output signal, e.g., taking into account the motion-sensor output signal. It is therefore possible to distinguish between an unintended input and an intended input at the touch-sensitive input unit particularly reliably.

According to a further advantageous embodiment, the value of the input intention may be ascertained from the output signal and from the at least one motion-sensor output signal. The value of the input intention may therefore be determined particularly robustly, in particular, compared with unwanted-signal components of the motion-sensor signal.

In a further advantageous embodiment, the value of the input intention may describe an input mode. By virtue of the output signal including fewer unwanted-signal components than the sensor signal, the temporal and/or spatial variation of the output signal may be analyzed with greater accuracy. As a result, it is possible, (e.g., for a capacitive input unit), to distinguish reliably between an input by different operating objects, for instance, between an input pen and/or a finger of an operator. The value of the input intention may here be adjusted, (e.g., scaled), for instance, according to a value assigned to a certain input type. For example, by analyzing the temporal and/or spatial variation of the output signal, it is possible to determine a type of the operating object that was used, in particular, for the input at the touch-sensitive input unit. Inputs by predetermined operating objects, (e.g., by an input pen), may be given a higher weighting than inputs by other operating objects, (e.g., a finger of an operator), depending on an area of use of the touch-sensitive input unit. This weighting of the input at the touch-sensitive input unit may advantageously be made possible by the fact that the value of the input intention describes the input type.

In a further advantageous embodiment, the medical apparatus may be controlled additionally by the value of the input intention. This may achieve particularly high certainty and reliability in the control of the medical apparatus. For example, the value of the input intention may be used to reduce and/or eliminate operating errors. Furthermore, the output signal may be adjusted, (e.g., scaled), for instance, according to the value of the input intention. This advantageously makes it possible to incorporate the determined input intention in the output signal.

A second aspect of the disclosure relates to a computer-implemented method for providing a trained function, including receiving a training sensor signal. The training sensor signal is time-resolved, and spatially resolved with respect to a, in particular predetermined, surface of a touch-sensitive input unit. In addition, the training sensor signal includes unwanted-signal components. The method additionally includes determining a reference output signal based on the training sensor signal, wherein the reference output signal is equivalent to the training sensor signal in the absence of unwanted-signal components. In addition, a training output signal is determined by applying the trained function to input data. The input data is based on the training sensor signal. In addition, the method includes adjusting at least one parameter of the trained function on the basis of a comparison of the reference output signal and the training output signal. In addition, the trained function is provided.

The time-resolved training sensor signal may include one or more inputs sequentially in time at the touch-sensitive input unit. Furthermore, the spatial resolution of the training sensor signal with respect to the surface of the touch-sensitive input unit may allow an input at the input unit to be located exactly. In particular, in combination with the time-resolution and spatial resolution of the training sensor signal, it is possible to describe inputs at the touch-sensitive input unit that include in particular a movement and/or input gesture.

The training sensor signal may be received by a training interface and/or a training processing unit. In particular, the reference output signal may be determined by the training interface and/or by the training processing unit. In addition, the training output signal may be determined by the training processing unit. Furthermore, the at least one parameter of the trained function may be adjusted by the training processing unit. In addition, the trained function may be provided by the training interface.

The training sensor signal may have all the attributes of the sensor signal that were described with reference to the method for providing an output signal, and vice versa. In particular, the training sensor signal may be a sensor signal. A training output signal and a reference output signal may have all the attributes of the output signal that were described with reference to the method for providing an output signal, and vice versa.

The proposed method may be used advantageously to provide a trained function, which may be used in the method for providing an output signal.

The training sensor signal and/or the unwanted-signal components of the training sensor signal may be simulated. In this process, different input types, (e.g., by different operating objects), at the touch-sensitive input unit may advantageously be simulated. It is also possible to simulate unwanted-signal components produced by noise and/or a fluid located on the surface of the touch-sensitive input unit. In particular, it is possible to simulate different fluid types, (e.g., water, blood, ultrasound gel, or combinations thereof), and different arrangements of fluids on the surface of the touch-sensitive input unit. It is also possible to simulate inputs at the touch-sensitive input unit, (e.g., by an operating object), in combination with objects that may produce unwanted-signal components.

A third aspect of the disclosure relates to a provider unit for providing an output signal. The provider unit includes a touch-sensitive input unit, a processing unit, and an interface. The touch-sensitive input unit is configured to detect a sensor signal, wherein the sensor signal is time-resolved, and spatially resolved with respect to a surface of the touch-sensitive input unit. The sensor signal includes unwanted-signal components. The processing unit is configured to determine an output signal by applying a trained function to input data. The input data is based on the sensor signal. The output signal is time-resolved, and spatially resolved with respect to the surface of the touch-sensitive input unit. At least one parameter of the trained function is based on a comparison with a sensor signal in the absence of unwanted-signal components. The interface is configured to provide the output signal.

The provider unit may be configured to perform the above-described methods for providing an output signal by a touch-sensitive input unit, and aspects of the methods. The provider unit may be configured to perform the proposed methods and aspects thereof by designing the interfaces and the processing unit to perform the relevant method acts.

A fourth aspect of the disclosure relates to a medical apparatus including a provider unit for providing an output signal, wherein the medical apparatus is configured to be controlled by the output signal. The medical apparatus may include a medical imaging device, (e.g., a magnetic resonance system, a medical X-ray apparatus, a computed tomography system, an ultrasound apparatus, a medical robotic device such as a catheter robot, a patient positioning device, a respiratory device, an anesthesia device, or a combination thereof).

A fifth aspect of the disclosure relates to a training system for providing a trained function. The training system includes a training interface and a training processing unit. The training interface and/or the training processing unit are configured to receive a training sensor signal. The training sensor signal is time-resolved, and spatially resolved with respect to a surface of a touch-sensitive input unit. The training sensor signal includes unwanted-signal components. The training interface and/or the training processing unit are additionally configured to determine a reference output signal on the basis of the training sensor signal. The reference output signal is equivalent to the training sensor signal in the absence of unwanted-signal components. The training processing unit is also configured to determine a training output signal by applying the trained function to input data, wherein the input data is based on the training sensor signal. The training processing unit is also configured to adjust at least one parameter of the trained function based on a comparison of the reference output signal and the training output signal. The training interface is also configured to provide the trained function.

The training system may be configured to perform the above-described methods for providing an output signal by a touch-sensitive input unit, and aspects of the methods. The training system is configured to perform these methods and aspects thereof by designing the training interface and the training processing unit to perform the relevant method acts.

A computer program product is also proposed, which may be loaded directly into a memory of a provider unit, and which contains program segments in order to perform all the acts of the method for providing an output signal by a touch-sensitive input unit or of aspects of the method when the program segments are executed by the provider unit.

A computer program product is also proposed, which may be loaded directly into a memory of a training system, and which contains program segments in order to perform all the acts of the method for providing a trained function or of one of the aspects of the method when the program segments are executed by the training system.

In addition, the disclosure relates to a computer-readable storage medium, on which are stored program segments which may be read and executed by a provider unit in order to perform all the acts of the method for providing an output signal by a touch-sensitive input unit or of aspects of the method when the program segments are executed by the provider unit.

The disclosure also relates to a computer-readable storage medium, on which are stored program segments which may be read and executed by a training system in order to perform all the acts of the method for providing a trained function or of one of the aspects of the method when the program segments are executed by the training system.

In addition, the disclosure relates to a computer program or a computer-readable storage medium, including a trained function provided by a method for providing a trained function or one of the aspects of the method.

An implementation based largely in software has the advantage that even provider units and/or training systems already in use may be easily upgraded by a software update in order to work in the manner according to the disclosure. The computer program product may include in addition to the computer program, if applicable, extra elements such as e.g. documentation and/or extra components, and also hardware components such as e.g. hardware keys (dongles etc.) for using the software.

BRIEF DESCRIPTION OF THE DRAWINGS

Exemplary embodiments of the disclosure are described in more detail below and illustrated in the drawings. The same reference signs are used for the same features in different figures, in which.

DETAILED DESCRIPTION

Figure 1:
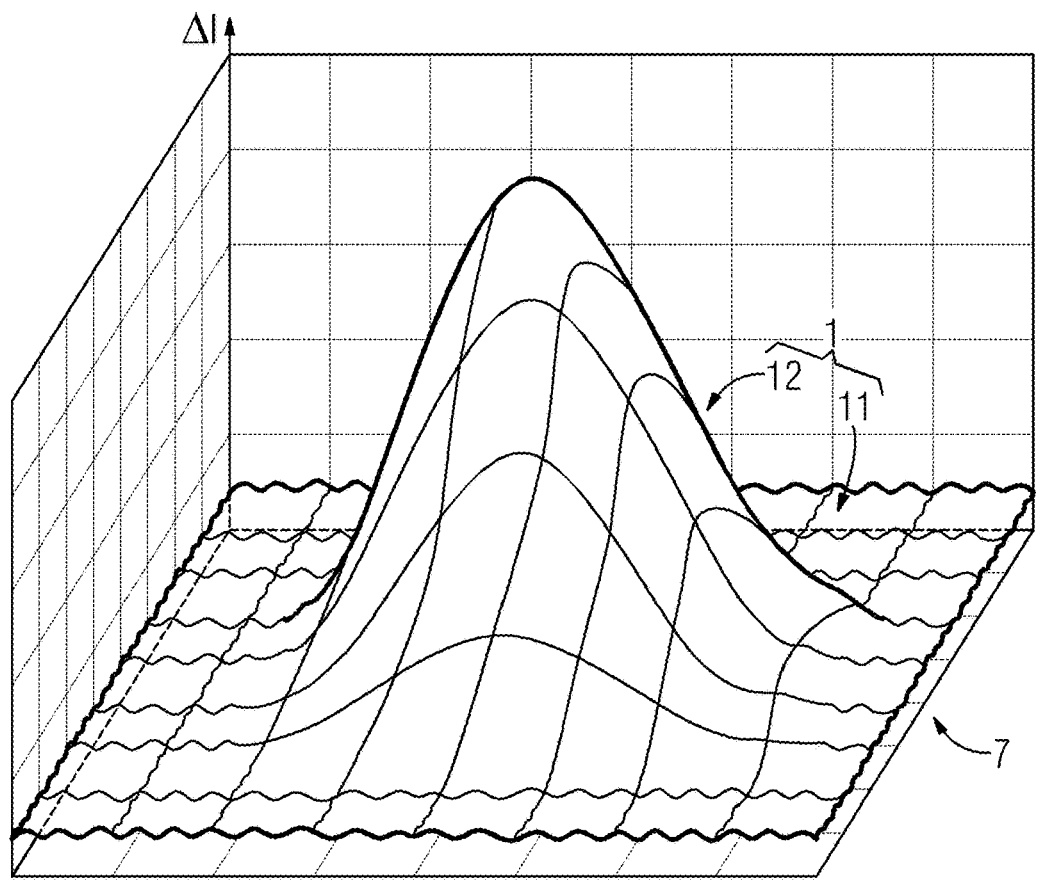
FIG. 1 depicts a schematic diagram of an example of a spatially resolved sensor signal at the time of an input at a touch-sensitive input unit.

FIG. 1 shows a schematic diagram of a spatially resolved sensor signal 1 at the time of an input at a touch-sensitive input unit 7. In this figure, the sensor signal 1 is shown schematically by way of example as a spatial profile of an intensity change ΔI, for instance, of a capacitance for a, in particular projected, capacitive input field, with respect to the surface of the touch-sensitive input unit 7. The sensor signal 1 here includes unwanted-signal components 11 and a wanted-signal component 12, which corresponds, (e.g., exclusively), to an input at the touch-sensitive input unit 7. The sensor signal 1 may be considered to be a sensor signal that contains errors resulting from superposition of the unwanted-signal components 11.

In addition, the surface of the touch-sensitive input unit 7 may be predetermined, e.g., by parameters. For example, the touch-sensitive input unit 7 may include a sensor (not shown here), which sensor is configured to detect a deformation, (e.g., a deflection), of the surface of the touch-sensitive input unit.

Figure 2:
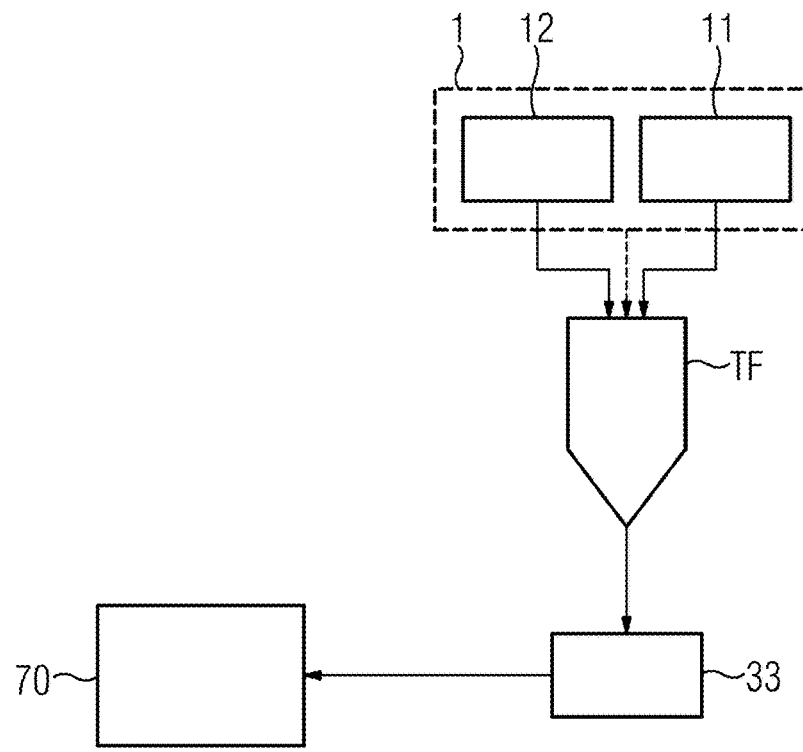
FIG. 2 depicts a first exemplary embodiment of a data flow in a method for providing an output signal by a touch-sensitive input unit.

FIG. 2 shows a first exemplary embodiment of a data flow in a method for providing an output signal by a touch-sensitive input unit 7. The trained function TF may advantageously include as input data the sensor signal 1, wherein the sensor signal 1 is time-resolved, and spatially resolved with respect to the surface of the touch-sensitive input unit 7. Furthermore, the sensor signal 1 may include unwanted-signal components 11.

In addition, an output signal 33 may be determined by applying the trained function TF to the input data. The output signal 33 is advantageously time-resolved, and spatially resolved with respect to the surface of the touch-sensitive input unit 7. In addition, at least one parameter of the trained function TF may be based on a comparison with a sensor signal in the absence of unwanted-signal components (not shown here). The trained function TF may be a function that maps a sensor signal 1 onto an output signal 33.

Figure 3:
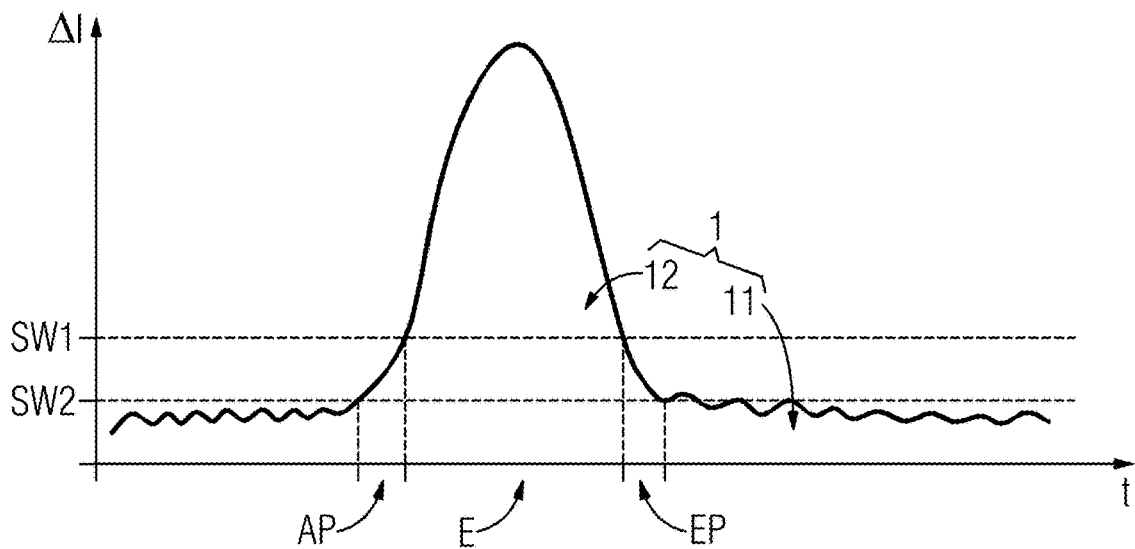
FIG. 3 depicts an example of a temporal variation of a sensor signal, which sensor signal additionally relates to a time period before and/or after an input at the touch-sensitive input unit.

FIG. 3 shows a temporal variation of a sensor signal 1, which sensor signal 1 additionally relates to a time period before and/or after an input at the touch-sensitive input unit 7. In the exemplary embodiment shown schematically in FIG. 3, the sensor signal 1 includes an unwanted-signal component 11, (e.g., produced by noise), and a wanted-signal component 12, which corresponds to an input at the touch-sensitive input unit 7. The temporal variation of the sensor signal 1 may be divided here into at least three stages AP, E, and EP, for instance in each case by a threshold value SW1 and SW2 of an intensity change ΔI at a stage transition. In particular, the temporal variation of the sensor signal 1 may relate to a time period before and/or after an input at the touch-sensitive input unit 7. The time period before and/or after the input at the touch-sensitive input unit 7 may equate to an approach time stage AP and/or a distancing time stage EP for an operating object for the input E at the touch-sensitive input unit 7. In particular, a first threshold value SW2 may be defined for distinguishing between a time period before the approach stage AP and/or after the distancing stage EP. In particular, if the intensity change ΔI lies above the first threshold value SW1 and below a second threshold value SW2, the sensor signal 1 may relate to the approach stage AP and/or the distancing stage EP. Moreover, an additional threshold value (not shown here) may be defined to demarcate between approach stage AP and distancing stage. As long as the intensity change ΔI lies above the second threshold value, the sensor signal 1 may be considered to be an input E.

While the sensor signal 1 in FIG. 3 includes an unwanted-signal component 11 and a wanted-signal component 12, which corresponds to an input E at the touch-sensitive input unit 7, it should be noted that the temporal variation of the sensor signal 1 still includes the unwanted-signal component 11 and the wanted-signal component 12 even given an intensity change ΔI above the first threshold value SW2 and the second threshold value SW1.

Figure 4:
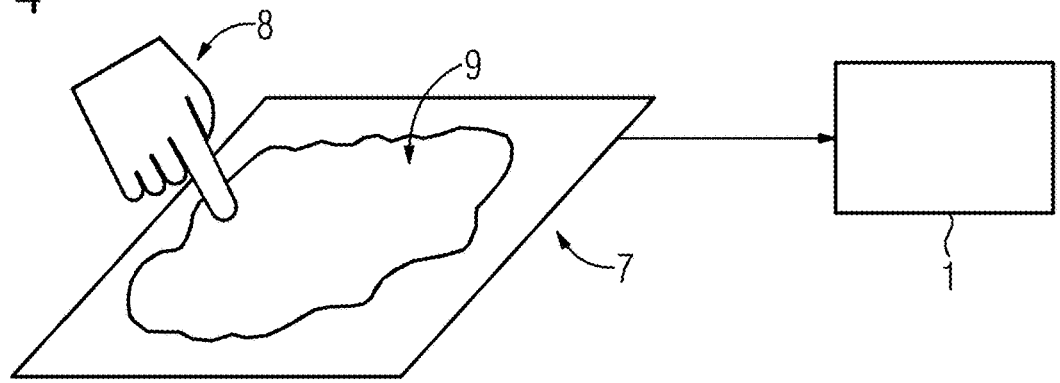
FIG. 4 depicts a schematic diagram of an example of a touch-sensitive input unit, on the surface of which is located a fluid.

FIG. 4 shows a schematic diagram of a touch-sensitive input unit 7, on the surface of which is located a fluid 9. The unwanted-signal components 11 may be produced here, for instance, by the, (e.g., electrically conducting), fluid 9 located on the surface of the touch-sensitive input unit.

In the event of an input E at the touch-sensitive input unit 7 by an operating object 8, (e.g., a finger of an operator and/or an input pen), the touch-sensitive input unit 7 may generate the sensor signal 1. The fluid 9 located on the surface of the touch-sensitive input unit 7 may produce an unwanted-signal component 11, e.g., even in the absence of a simultaneous input E. In the event of an input at the touch-sensitive input unit 7, e.g., irrespective of a position of the fluid 9 located on the surface of the touch-sensitive input unit 7, the sensor signal 1 may include an unwanted-signal component 11 and a wanted-signal component 12, which corresponds to the input E.

Figure 5:
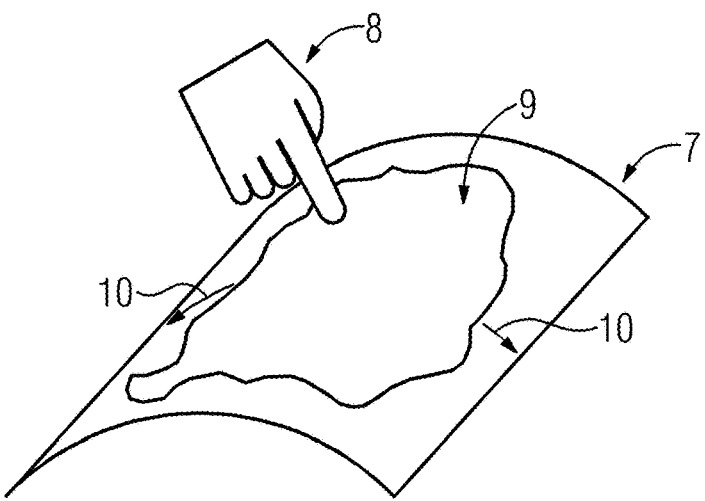
FIG. 5 depicts a schematic diagram of an example of a touch-sensitive input unit having a curved surface, on which is located a fluid.

FIG. 5 shows a schematic diagram of a touch-sensitive input unit 7 having a curved surface, on which is located a fluid 9. In this case, the unwanted-signal component 11 may have a temporal variation, which describes a spreading movement and/or a flow movement 10 of the, (e.g., electrically conducting), fluid 9 on the surface of the touch-sensitive input unit 7. The spreading movement and/or flow movement of the fluid 9 on the surface of the touch-sensitive input unit may produce in particular a change over time in the unwanted-signal component 11. In combination with the temporal variation of the wanted-signal component 12, which corresponds to an input E by an operating object 8 at the touch-sensitive input unit 7, a spatial and temporal variance may arise between the unwanted-signal component 11 and the wanted-signal component 12.

Advantageously, the surface of the touch-sensitive input unit 7 is predetermined, in particular, by parameters. Therefore, the unwanted-signal component 11, (e.g., produced by the spreading movement and/or flow movement 10 of the fluid 9 located on the surface of the touch-sensitive input unit 7), may be ascertained from the position and/or spatial extent of the fluid 9.

In addition, the sensor signal 1 may include an unwanted-signal component 11 from an electromagnetic field at least adjoining the surface of the touch-sensitive input unit 7.

Figure 6:
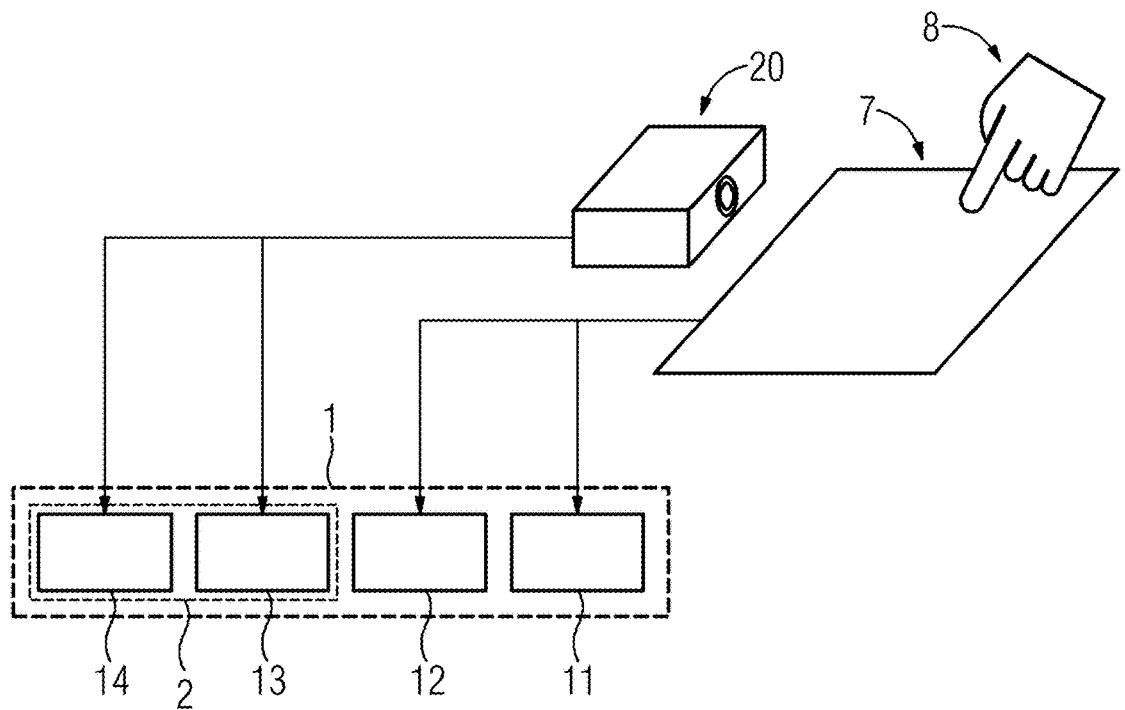
FIG. 6 depicts a schematic diagram of an example of a touch-sensitive input unit having a motion sensor.

FIG. 6 shows a schematic diagram of a touch-sensitive input unit 7 having a motion sensor 20. In this case, the sensor signal 1 may additionally include at least one motion-sensor signal 2. In addition, at least one motion-sensor signal 2 may include unwanted-signal components 13 and a motion-sensor signal component 14, which corresponds to a movement and/or alteration at the touch-sensitive input unit 7 detected by the motion sensor 20. For example, the motion sensor 20 may be configured to detect a movement of the operating object 8 during an input E at the touch-sensitive input unit 7. Then, the motion sensor 20 may generate a corresponding motion-sensor signal 2. In addition, the motion sensor 20 may be configured to detect an alteration such as a deflection, (e.g., at the surface), of the touch-sensitive input unit. The unwanted-signal components 13 may be produced, for example, by noise and/or a fluid 9 located on the surface of the touch-sensitive input unit 7. In particular, the motion sensor 20 and the motion-sensor signal 2 generated by the motion sensor 20 may be used to validate an input E at the touch-sensitive input unit 7.

Figure 7:
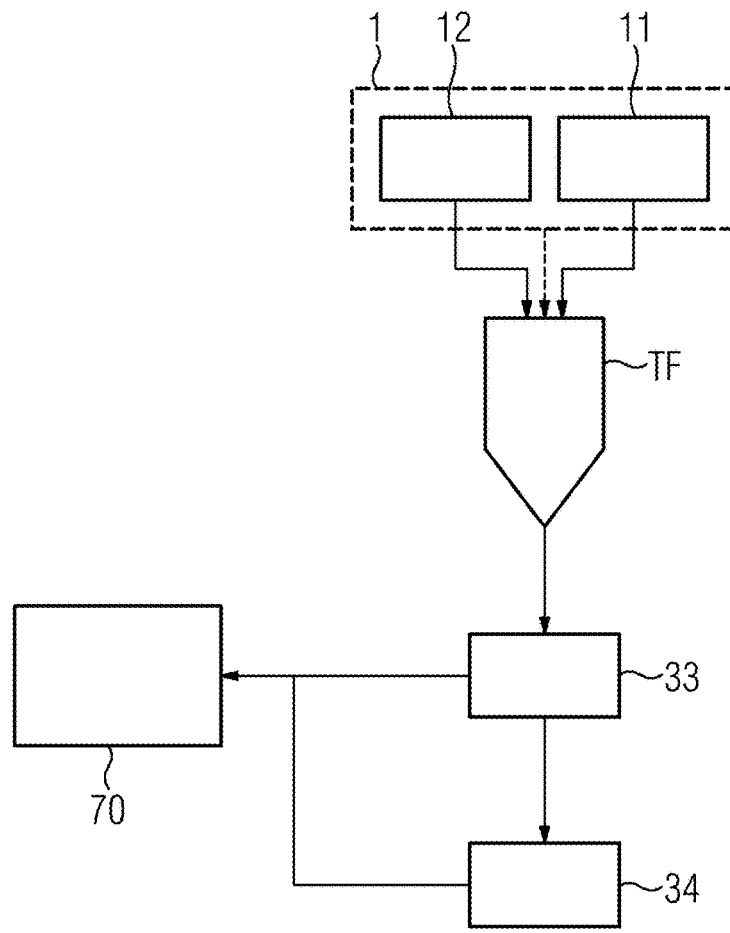
FIGS. 7 and 8 depict further exemplary embodiments of the data flow in a method for providing an output signal by a touch-sensitive input unit.

FIG. 7 shows a further exemplary embodiment of the data flow in a method for providing an output signal 33 by the touch-sensitive input unit 7. In this case, a value of an input intention 34 may be ascertained from the output signal 33. The value of the input intention may advantageously describe an input type, for instance, a specification of an operating object. Furthermore, the medical apparatus 70 may be controlled by the value of the input intention 34 in addition to the output signal 33.

Figure 8:
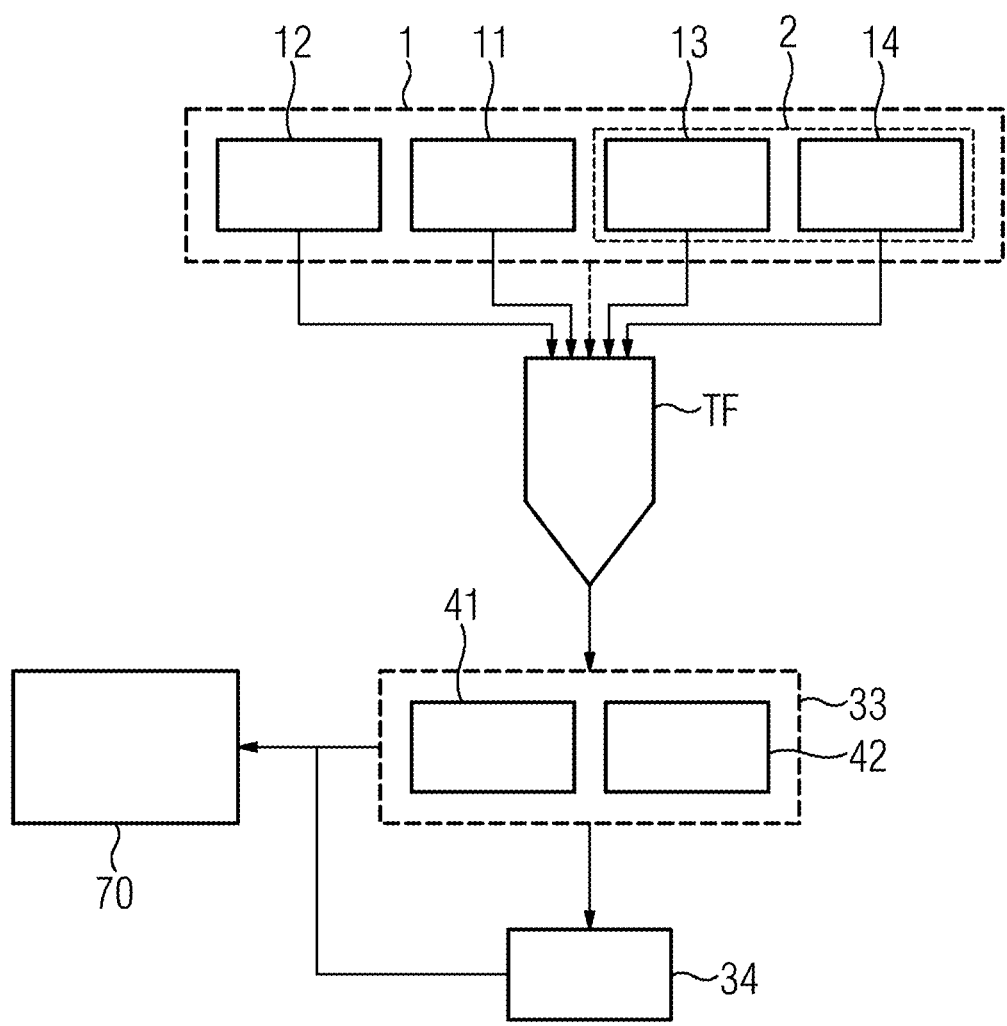

FIG. 8 shows a further exemplary embodiment of the data flow in a method for providing an output signal 33 by the touch-sensitive input unit 7. In this case, the sensor signal 1 may additionally include at least one motion-sensor signal 2. The at least one motion-sensor signal 2 may again include unwanted-signal components 13. In addition, the output signal 33 may include an output-signal component 31 and at least one motion-sensor output signal 42. The output-signal component 41 may advantageously be assigned to the wanted-signal component 12, which corresponds to an input E at the touch-sensitive input unit 7 and may be generated by the input unit 7. In addition, the motion-sensor output signal 42 may advantageously be assigned to the motion-sensor signal component 14, which corresponds to an input E at the touch-sensitive input unit 7, which input is detected by the motion sensor 20 and in particular has been generated by the motion sensor 20. Furthermore, the value of the input intention 34 may be ascertained from the output signal 33, e.g., taking into account the at least one motion-sensor output signal 42. Moreover, the medical apparatus 70 may be controlled by the output signal 33 and the value of the input intention 34.

Figure 9:
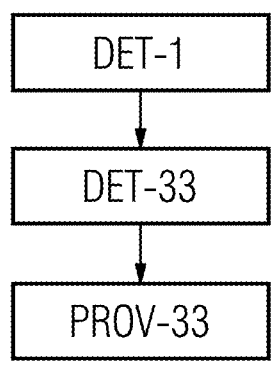
FIG. 9 depicts a flow diagram of an exemplary method for providing an output signal by a touch-sensitive input unit.

FIG. 9 shows a flow diagram of a method for providing an output signal 33 by a touch-sensitive input unit 7. The first act of the depicted method may include detecting DET-1 the sensor signal, in particular, by an interface IF and/or a processing unit CU. The sensor signal 1 may be time-resolved, and spatially resolved with respect to the surface of the touch-sensitive input unit 7. Furthermore, the sensor signal 1 may include unwanted-signal components 11. The subsequent act of the proposed method may include determining DET-33 the output signal 33 by applying the trained function TF to input data, in particular, by the processing unit CU. The input data may be based on the sensor signal 1. In addition, the output signal 33 may be time-resolved, and spatially resolved with respect to the surface of the touch-sensitive input unit 7. Moreover, at least one parameter of the trained function TF may be based on a with a sensor signal in the absence of unwanted-signal components (not shown here). The trained function TF may here be a neural network, in particular a convolutional neural network (CNN) or a network including a convolutional layer. In the final act PROV-33 of the exemplary embodiment shown, the output signal 33 may be provided, e.g., by the interface IF. The providing PROV-33 of the output signal 33 may include storing and/or transferring the output signal, for instance, in order to control the medical apparatus 70.

Figure 10:
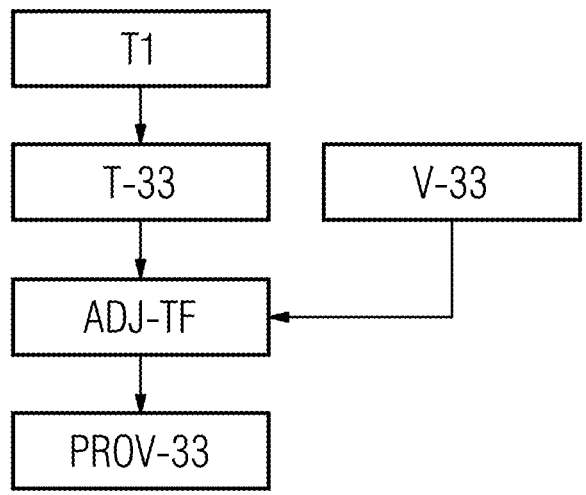
FIG. 10 depicts a flow diagram of an exemplary method for providing a trained function.

FIG. 10 shows a flow diagram of a method for providing a trained function TF. In this case, in a first act T1, a training sensor signal may be received, (e.g., by a training interface TIF and/or a training processing unit TCU). The training sensor signal may be time-resolved, and spatially resolved with respect to the surface of the touch-sensitive input unit 7. In addition, the training sensor signal may include unwanted components.

In a further act V-33, a reference output signal may be determined based on the training sensor signal, in particular by the training interface TIF and/or the training processing unit TCU. The reference output signal may be equivalent to the training sensor signal in the absence of unwanted-signal components.

A further act T-33 may include determining a training output signal by applying the trained function TF to input data, in particular, by the training processing unit TCU. The input data may be based on the training sensor signal. The trained function TF may be a neural network, in particular, a convolutional neural network or a network including a convolutional layer.

In a further act ADJ-TF, at least one parameter of the trained function may be adjusted, in particular, by the training processing unit TCU, based on a comparison of the reference output signal and the training output signal. In this exemplary embodiment, the trained function TF may include an artificial neural network. The adjusting of the artificial neural network may include adjusting at least one edge weight of the artificial neural network. In addition, the adjustment may be based on the backpropagation algorithm.

In a final act PROV-TF, the trained function TF may be provided, in particular, by the training interface TIF and/or the training processing unit TCU. In the exemplary embodiment shown, the trained function may be stored. Alternatively, the trained function (or one or more parameters thereof) may also be displayed or transmitted for further processing.

Figure 11:
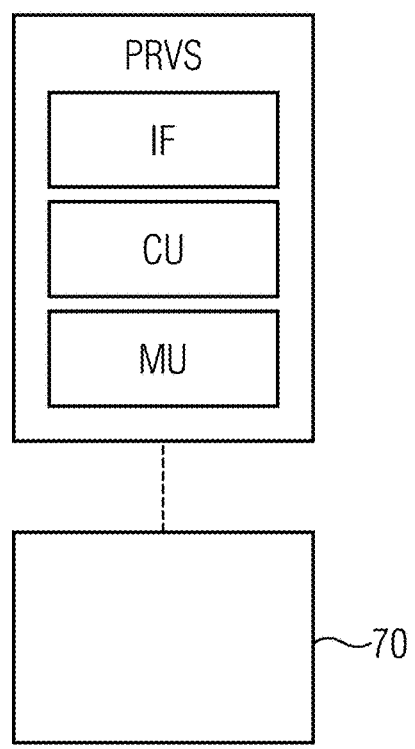
FIG. 11 depicts an exemplary embodiment of a provider unit.
Figure 12:
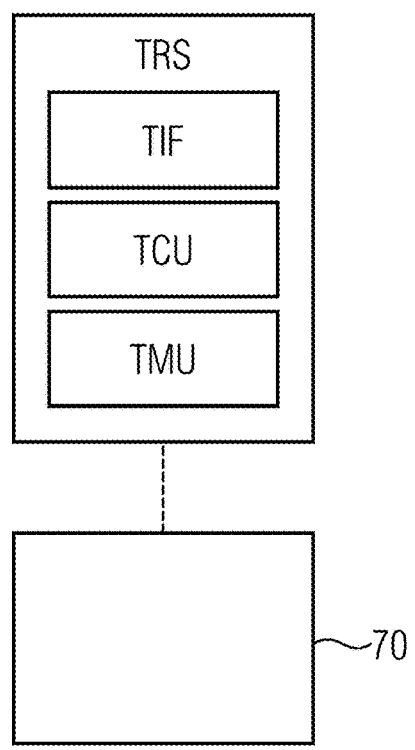
FIG. 12 depicts an exemplary embodiment of a training system.

FIG. 11 shows a provider unit PRVS. FIG. 12 shows a training system TRS. The depicted provider unit PRVS is configured to perform a method according to the disclosure for providing a difference image dataset DD. The depicted training system is configured to perform a method according to the disclosure for providing a trained function TF. The provider unit PRVS includes an interface IF, a processing unit CU, and a memory unit MU. The training system TRS includes a training interface TIF, a training processing unit TCU, and a training memory unit TMU.

The provider unit PRVS and/or the training system TRS may be a computer, a microcontroller, or an integrated circuit. Alternatively, the provider unit PRVS and/or the training system TRS may be a real or virtual interconnection of computers (a real interconnection is referred to as a "cluster" and a virtual interconnection is referred to as a "Cloud"). The provider unit PRVS and/or the training system TRS may also be embodied as a virtual system, which is implemented on a real computer or a real or virtual interconnection of computers (virtualization).

An interface IF and/or a training interface TIF may be a hardware or software interface (for instance PCI bus, USB, or FireWire). A processing unit CU and/or a training processing unit TCU may include hardware elements or software elements, for instance a microprocessor or what is known as a field programmable gate array (FPGA). A memory unit MU and/or a training memory unit TMU may be implemented as a non-permanent main memory (random access memory or RAM for short) or as a permanent mass storage device (hard disk, USB stick, SD card, solid state disk).

The interface IF and/or the training interface TIF may include in particular a plurality of sub-interfaces, which implement different acts of the respective methods. In other words, the interface IF may also be regarded as a multiplicity of interfaces IF, and the training interface TIF may also be regarded as a multiplicity of training interfaces TIF. The processing unit CU and/or the training processing unit TCU may include in particular a plurality of sub-processing units, which implement different acts of the respective methods. In other words, the processing unit CU may also be regarded as a multiplicity of processing units CU, and the training processing unit TCU may also be regarded as a multiplicity of training processing units TCU.

The schematic diagrams contained in the described figures are not shown to scale in any way and do not depict relative sizes.

Finally it should be reiterated that the methods described in detail above and the presented devices are merely exemplary embodiments, which may be modified by a person skilled in the art in many ways without departing from the scope of the disclosure. In addition, the use of the indefinite article "a" or "an" does not rule out the possibility of there also being more than one of the features concerned. Likewise, the term "unit" does not exclude the possibility that the components in question include a plurality of interacting sub-components, which may also be spatially distributed if applicable.

Although the disclosure has been illustrated and described in greater detail by the exemplary embodiments, the disclosure is not restricted by these exemplary embodiments. Other variations may be derived herefrom by the person skilled in the art, without departing from the scope of protection of the disclosure. It is therefore intended that the foregoing description be regarded as illustrative rather than limiting, and that it be understood that all equivalents and/or combinations of embodiments are intended to be included in this description.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

The invention claimed is:

1. A computer-implemented method for providing an output signal by a touch-sensitive input unit, the method comprising:
   detecting a sensor signal, wherein the sensor signal is time-resolved, and spatially resolved with respect to a surface of the touch-sensitive input unit, and wherein the sensor signal comprises unwanted-signal components,
   determining the output signal by applying a trained function to input data, wherein the input data is based on the sensor signal, wherein the output signal is time-resolved, and spatially resolved with respect to the surface of the touch-sensitive input unit, and wherein at least one parameter of the trained function is based on a comparison with a sensor signal in an absence of the unwanted-signal components; and
   providing the output signal.

2. The method of claim 1, wherein the sensor signal has a temporal variation that relates to a time period before and/or after an input at the touch-sensitive input unit.

3. The method of claim 2, wherein the unwanted-signal components are produced by noise, by a fluid located on the surface of the touch-sensitive input unit, or a combination thereof.

4. The method of claim 3, wherein the fluid is an electrically conducting fluid.

5. The method of claim 1, wherein the unwanted-signal components are produced by noise, by a fluid located on the surface of the touch-sensitive input unit, or a combination thereof.

6. The method of claim 5, wherein the fluid is an electrically conducting fluid.

7. The method of claim 5, wherein an unwanted-signal component of the unwanted-signal components has a temporal variation that describes a spreading movement, a flow movement of the fluid on the surface of the touch-sensitive input unit, or a combination thereof.

8. The method of claim 7, wherein the fluid is an electrically conducting fluid.

9. The method of claim 1, wherein an unwanted-signal component of the unwanted-signal components is from an electromagnetic field at least adjoining the surface of the touch-sensitive input unit.

10. The method of claim 1, wherein the sensor signal further comprises at least one motion-sensor signal,
    wherein the at least one motion-sensor signal comprises unwanted-signal components,
    wherein the output signal comprises at least one motion-sensor output signal, and
    wherein the at least one motion-sensor output signal comprises fewer unwanted-signal components than the unwanted-signal components of the at least one motion-sensor signal.

11. The method of claim 10, further comprising:
    ascertaining a value of an input intention from the output signal.

12. The method of claim 11, further comprising:
    controlling a medical apparatus using the value of the input intention.

13. The method of claim 1, wherein the output signal is used to control a medical apparatus.

14. The method of claim 1, further comprising:
ascertaining a value of an input intention from the output signal.

15. The method of claim 14, wherein the value of the input intention describes an input type.

16. The method of claim 15, further comprising:
controlling a medical apparatus using the value of the input intention.

17. The method of claim 14, further comprising:
controlling a medical apparatus using the value of the input intention.

18. A computer-implemented method for providing a trained function, the method comprising:
receiving a training sensor signal, wherein the training sensor signal is time-resolved, and spatially resolved with respect to a surface of a touch-sensitive input unit, and wherein the training sensor signal comprises unwanted-signal components;
determining a reference output signal based on the training sensor signal, wherein the reference output signal is equivalent to the training sensor signal in an absence of the unwanted-signal components;
determining a training output signal by applying the trained function to input data, wherein the input data is based on the training sensor signal;
adjusting at least one parameter of the trained function based on a comparison of the reference output signal and the training output signal; and
providing the trained function.

19. A device comprising:
a touch-sensitive input unit configured to detect a sensor signal, wherein the sensor signal is time-resolved, and spatially resolved with respect to a surface of the touch-sensitive input unit, and wherein the sensor signal comprises unwanted-signal components;
a processor configured to determine an output signal by applying a trained function to input data, wherein the input data is based on the sensor signal, wherein the output signal is time-resolved, and spatially resolved with respect to the surface of the touch-sensitive input unit, and wherein at least one parameter of the trained function is based on a comparison with a sensor signal in an absence of the unwanted-signal components; and
an interface configured to provide the output signal.

20. A medical apparatus comprising:
a touch-sensitive input unit configured to detect a sensor signal, wherein the sensor signal is time-resolved, and spatially resolved with respect to a surface of the touch-sensitive input unit, and wherein the sensor signal comprises unwanted-signal components;
a processor configured to determine an output signal by applying a trained function to input data, wherein the input data is based on the sensor signal, wherein the output signal is time-resolved, and spatially resolved with respect to the surface of the touch-sensitive input unit, and wherein at least one parameter of the trained function is based on a comparison with a sensor signal in an absence of the unwanted-signal components; and
an interface configured to provide the output signal,
wherein the medical apparatus is configured to be controlled by the output signal.

* * * * *